United States Patent [19]

Müller et al.

[11] 4,345,339
[45] Aug. 24, 1982

[54] BIOLOGICALLY IMPLANTABLE MEMBER FOR A TENDON AND/OR LIGAMENT

[75] Inventors: Arnold Müller, Bachs; Gerhard Bröckel, Seuzach, both of Switzerland

[73] Assignee: Sulzer Brothers Limited, Winterthur, Switzerland

[21] Appl. No.: 265,067

[22] Filed: May 19, 1981

[30] Foreign Application Priority Data

Jun. 3, 1980 [CH] Switzerland .................... 4278/80

[51] Int. Cl.³ .............................................. A61F 1/24
[52] U.S. Cl. ............................................. 3/1; 128/92 C; 128/92 B; 128/92 D
[58] Field of Search ............................. 3/1, 1.9–1.911; 128/92 C, 92 B, 92 D

[56] References Cited

U.S. PATENT DOCUMENTS

| | | | |
|---|---|---|---|
| 3,176,316 | 4/1965 | Bodell | 3/1 |
| 3,513,484 | 5/1970 | Hausner | 3/1 |
| 3,797,047 | 3/1974 | Pillet | 3/1 |
| 3,805,300 | 4/1974 | Tascon-Alonso et al. | 3/1 |
| 3,896,500 | 7/1975 | Rambert et al. | 3/1 |
| 4,187,558 | 2/1980 | Dahlen et al. | 3/1 |
| 4,246,660 | 1/1981 | Wevers | 3/1 |

*Primary Examiner*—Ronald L. Frinks
*Attorney, Agent, or Firm*—Kenyon & Kenyon

[57] ABSTRACT

The tendon and/or ligament substitute is inelastic in the longitudinal direction and is formed of a round rope having a core filament and outer filaments of smaller diameter surrounding the core filament. Each filament is encased in a tube to reduce abrasion and a cover holds the various filaments together. The construction of the filaments insures an increase in elasticity from the inside to the outside as required for biological-medical reasons.

12 Claims, 9 Drawing Figures a)

b)

c)

d)

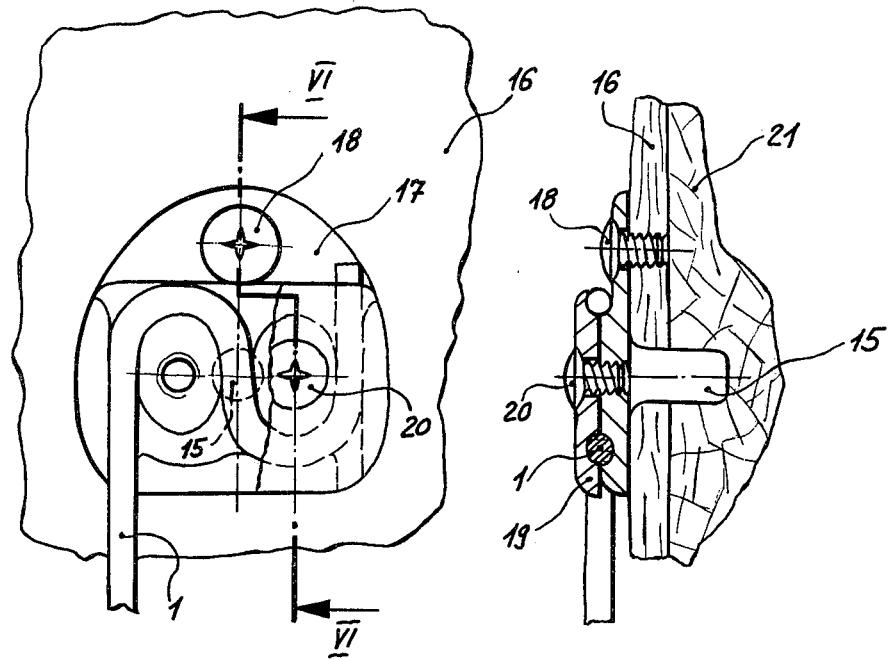

BIOLOGICALLY IMPLANTABLE MEMBER FOR A TENDON AND/OR LIGAMENT

This invention relates to a biologically implantable member for a tendon and/or ligament.

As is known, natural ligaments and tendons are composed of a plurality of single-or tendinous fibers, each of which pulls from a determined origin to an exactly corresponding insertion point. In a movement, the corresponding attachment surfaces maintain their center distance and change their inclination to each other, thus requiring a certain displacement of the fibers relative to each other. Since those fibers which have their origin at the farthest points of one surface of insertion, are attached at the nearest point of the other, this has the result that the fiber unit performs a rotation about the longitudinal axis.

This difficult, but highly resistant, biological structure can not be simulated in the same manner with technical means. However, a good approximation should be obtained if the artificial substitute ligament made of allo-plastic materials has a round structure with a bending elasticity which increases from the core to the outside.

In addition to substitutes of tendons and ligaments from the body's own tissue, a number of allo-plastic materials, like steel wires, synthetic-, silk- or carbon filaments have already been used in the form of ropes or tissues as a substitute for torn ligaments, such as described in DOS No. 28 36 921. The present substitute ligaments differ from natural ligaments primarily by a certain elasticity in the longitudinal direction. Beyond that, it has not been possible to keep the abrasion, caused in the above-mentioned displacement of the single "fibers" relative to each other, within tolerable limits.

Accordingly, it is an object of the invention to provide a biologically implantable member which can be used for a tendon and/or ligament.

It is another object of the invention to provide an artificial ligament which is substantially inelastic in a longitudinal direction and which provides a round structure with a bending elasticity which increases from the core to the outside.

It is another object of the invention to provide an artificial ligament composed of longitudinal filaments wherein abrasion of the filaments on each other is reduced to a minimum.

Briefly, the invention provides a member which can be used as a tendon and/or ligament substitutes for implantation in an animal or human body and which consists of a plurality of filaments which extend substantially in the longitudinal direction of the ligament.

The biologically implantable member is comprised of at least one rope having a core filament, at least one ring of outer filaments surrounding the core filament and being of smaller diameter than the core filament, a plurality of tubes which encase the respective filaments in relatively longitudinally moveable relation and a cover encircling the ring of encased outer filaments. The construction of the member is such that the rope has an outwardly increasing bending elasticity from the core filament.

The term "filament" comprises in the present case all linear structures of natural yarns, chemical fibers, metals, carbon and, if necessary, ceramic materials and minerals. The substances used as filaments are selected, as in other body implants, primarily on the basis of biological-medical suitability, and furthermore on the basis of their physical properties, such as strength and/or elasticity.

By embedding each filament in a tube which consists preferably of a webbing or braiding of natural silk but which can also consist of a plastic tube, is known, for example, in electrical engineering arts as an insulating tube, abrasion at the various core and outer filaments is avoided. By a suitable selection of the material, it is furthermore possible to make the ligaments inelastic in the longitudinal direction for the stresses which may occur in use. For example, the filaments can consist of a wire of metal or metal alloy with diameters of 0.1 to 1 millimeter (mm) for the core filaments and of 0.05 to 0.5 millimeters (mm) for the outer filaments.

The use of individual, relatively thin filaments ensures great bending elasticity of the ligament, despite the relative inelasticity of the filaments in the longitudinal direction, and extensibility primarily in a direction perpendicular to the longitudinal axis, which is particularly necessary under stress conditions.

An axially-symmetrical concentric structure of the rope consisting of a core filament and surrounding outer filaments, which have a smaller diameter than the core filament, ensures the required outwardly increasing elasticity.

In order to obtain stronger ligaments with an outwardly increasing elasticity, the ligament may be made as a rope with more than one sheathing or ring of outer filaments around the core. In this case, the diameters of the outer filaments decrease from the core to the outside from ring to ring. In addition, covers may be provided between the individual rings of the outer filaments to reduce abrasion.

In providing ligaments of greater strength, the required properties can also be achieved if a rope serves as a module unit for a cable, where the individual module units or ropes are likewise arranged according to the principle of a core surrounded by at least one ring and are combined in at least one cable cover. In these cases, it is advisable to arrange a different number, e.g. 3 to 6 ropes in the ring or rings of the sheathing. It is also possible to use different ropes for the construction of the core rope and the sheathing ropes of the cable. For example, a rope can be used as a core rope which itself has several rings of outer filaments about a core while ropes with only one ring of outer filaments serve as sheathing ropes.

In the same manner, several cables can be combined to form ligaments which are to be exposed to greater stresses. In this case, the outwardly increasing elasticity can be achieved, for example, by using a cable with a large number of ropes in an outer ring or sheathing as a core and a cable with fewer ropes in its sheathing as a sheathing cable for the core cable.

Based on the above-mentioned rotation about the longitudinal axis, which the natural fiber unit performs during use, it may be of advantage if the outer filaments and/or sheathing ropes or-cables are wound helically about their core.

These and other objects and advantages of the invention will become more apparent from the following detailed description taken in conjunction with the accompanying drawings in which:

FIG. 5 illustrates a top view of one embodiment of an anchoring element for fastening a ligament according to the invention to a bone; and FIG. 6 illustrates a view taken on line VI—VI of FIG. 5.

Figure 1:
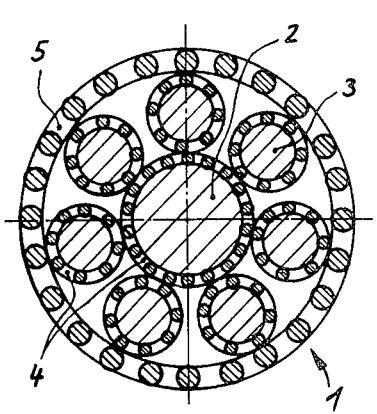
FIG. 1 illustrates a cross-sectional view of a member constructed as a rope in accordance with the invention.

Referring to FIG. 1, the biologically implantable member which can be used for tendons and/or ligaments is comprised of a rope 1 having a core filament 2, a ring of outer filaments 3 surrounding the core filament 2 and a cover 5 encircling the ring of outer filaments 3. Each individual filament 2, 3 is encased in a tube 4 in a relatively longitudinally movable relation. The core filament 2 is made, for example of a wire of a metal alloy which is suitable for implantation in a human or animal, such as a CoNiCrMoTi wrought alloy. The outer filaments 3 are made of the same material as the core filament 2 and are disposed about the core filament 2 in a concentric and axially symmetric relation. The outer filaments 3 are also helically disposed about the core filament 2 at a slight angle while extending longitudinally of the core filament 2. The tubes 4 are made of any suitable material so as to prevent or at least reduce abrasion of the filaments 2, 3. These tubes 4 absorb the stresses caused during a relative longitudinal displacement between the individual "fibers" of the ligament or the rope 1. The tubes 4 may be made as a braiding for example of a suitable textile material or of natural silk.

The cover 5 which serves to enclose the encased filaments 2, 3 ensures the mechanical cohesion and relative position of the outer filaments 3 about the core filament 2.

Figure 2:
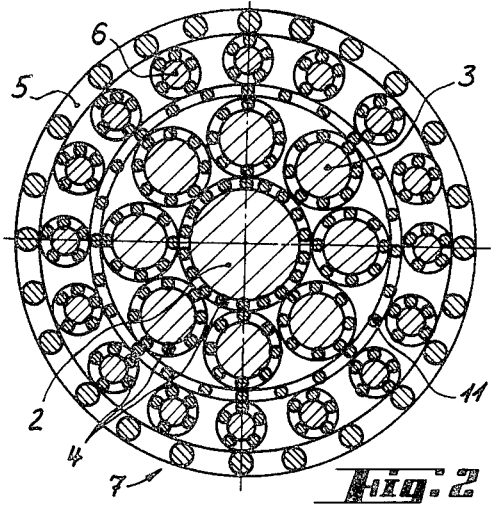
FIG. 2 illustrates a cross-sectional view of a modified rope-like member constructed in accordance with the invention.

Referring to FIG. 2, wherein like reference characters indicate like parts as above, the member may be made of a rope 7 having a plurality e.g. two, rings disposed in concentric relation with the core filament 2. As indicated, the inner ring has filaments 3 of smaller diameter than the core filament 2 while the outer ring has filaments 6 of smaller diameter than the filaments 3. In addition to the outer cover 5, an additional cover 11 is provided between the rings of outer filaments 3, 6 in order to fix the outer filaments 3, 6 geometrically in the individual rings. These additional covers 11 are made as a braiding of textile material to facilitate and simplify the twisting of the outer filaments 3, 6 about the core filament 2.

By way of example, the core filament 2 may be of a diameter of between 0.1 to 1.0 millimeter while the outer filaments 3, 6 have diameters of between 0.05 to 0.5 millimeters. The relationship between the diameter of the core filament and those of the respective rings of outer filaments 3, 6 is such that the diameters of the filaments 3, 6 decrease outwardly of the core element 2 in order to increase the bending elasticity of the rope 7 from the inside to the outside.

The tubes 4 which are formed, for example as a tubular braiding or webbing can be fabricated so that the density of the tube for the core filament is greater than the density of the tubes for the outer filaments 3, 6 and the cover 5. A preferred material for the tubes 4 and cover 5 is natural silk. Alternatively, from a manufacturing viewpoint, the various filaments 2, 3, 6 may be covered with plastic, for example in the manner of the insulation of an electrical line. The coating of the filaments with such a plastic may be carried out by dipping the filaments into a bath of a suitable plastic. The outer cover 5 may also be made of such a plastic.

It is to be noted that the various outer filaments 3, 6 are shown at relatively large spacings. However, these filaments can be packed as close as possible.

Figure 3:
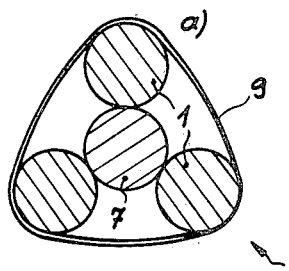
FIGS. 3a to 3d illustrate various cross-sections of cables constructed in accordance with the invention.
Figure 3:
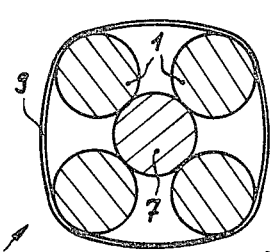

Although a rope 1, 7 can be used directly as a ligament or tendon substitute either can be used as a module unit for the construction of a ligament with a higher load capacity. For example as shown in FIG. 3, one rope 7 may be disposed as a core rope while a plurality of ropes 1 are disposed about the core rope with a cover 9 encircling the ropes 1, 7 to form a cable 8. As above, the ropes 1 surround the core rope 7 concentrically and axially symmetrically. Further, the ropes 1 may number three (FIG. 3a), four (FIG. 3b), five (FIG. 3c) or six (FIG. 3d) or up to eight, for example, depending on the difference in the diameters between the core rope 7 and the sheathing ropes 1. The required outwardly increasing bending elasticity is ensured, for example, by using a stiffer rope 7 as the core rope and more elastic ropes 1 as the sheathing ropes. The elasticity of the outer ring can also be varied to a certain extent by the use of a different number of ropes 1 in the outer ring. The fewer the ropes 1 in the ring, the greater is the elasticity of the cable 8 in the outer region. Thus, as indicated, the bending elasticity decreases at the outside region with an increase in the number of ropes 1 in the outer ring.

As above, the cable cover 9 which encases the ropes 1, 7 may be formed of a natural silk braiding.

As in the case of the ropes, the cables 8 may also be assembled using a core rope and two or more rings of sheathing ropes.

Figure 4:
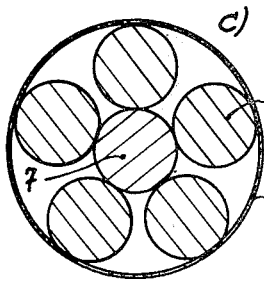
FIG. 4 illustrates a cross-sectional view of a ligament made of several cables in accordance with the invention.
Figure 4:
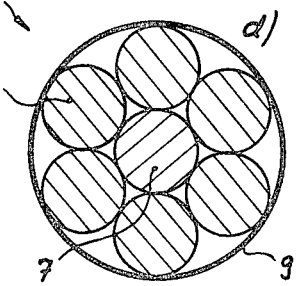
Figure 4:
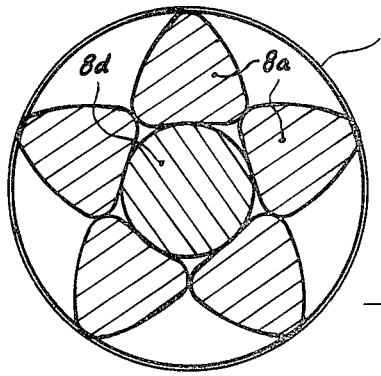

Referring to FIG. 4, for ligaments which are subjected to extreme stresses, a plurality of cables 8 can be combined to form a ligament. For example, as shown, a core cable 8d corresponding to FIG. 3d may be used with sheathing cables 8a formed in the manner as shown in FIG. 3a. These cables 8a, 8d may also be encased within a textile cover 10 formed of a natural silk braiding or plaiting.

Referring to FIG. 5, in order to anchor the substitute ligament on a bone, use is made of any suitable anchoring unit. To this end, the anchoring unit includes a plate 17 which carries a pin 15 which can be inserted through the cortical layer 16 of the bone into a spongy layer 21. The plate 17 is secured to the bone by one or more screws 18 which are threaded into the cortical layer 16. In addition, a cover 20 is mounted over the plate 17 and is held thereon by one or more screws 20. The plate 17 and cover 20 together form two bollard-type posts, for example similar to those used for mooring ships on landing piers. As shown in FIG. 5, a ligament 1 to be secured in place is wound around the posts and clamped between the cover 19 and plate 17 by tightening of the screws 20.

It is to be noted that the artificial ligaments can be anchored on a bone in any other suitable manner. Further, the various elements of the ligament may be made of any suitable materials.

The invention thus provides a substitute ligament which can simulate the rotation of a natural ligament during use to a high degree.

The invention further provides a member which can be used as a tendon or ligament of round structure with a bending elasticity which increases from the core to the outside in order to simulate as close as possible the elasticity of a natural tendon or ligament.

What is claimed is:

1. A biologically implantable member for tendons and ligaments comprising
at least one rope having a core filament; a first tube encasing said filament therein in relatively longitudinally movable relation; at least one ring of outer filaments surrounding said first tube and said core filament, each said outer filament being of smaller diameter than said core filament; a plurality of tubes, each said tube encasing a respective outer filament therein in relatively longitudinally movable relation; and a cover encircling said ring whereby said rope has an outwardly increasing bending elasticity from said core filament.

2. A member as set forth in claim 1 which comprises a plurality of said ropes, one of said ropes being disposed as a core rope and others of said ropes being disposed in at least one ring about said core rope and a cover encircling said ropes to form a cable.

3. A member as set forth in claim 2 which comprises a plurality of said cables, one of said cables being disposed as a core cable and others of said cables being disposed in at least one ring about said core cable, each said other cable having a different number of ropes therein from the remainder of said other cables and a cover surrounding said cables.

4. A member as set forth in claim 3 wherein each of said tubes and said covers is a braiding or plaiting.

5. A member as set forth in claim 4 wherein each braiding or plaiting is made of natural silk.

6. A member as set forth in claim 1 wherein each of said tubes and said cover is a braiding or plaiting.

7. A member as set forth in claim 6 wherein each braiding or plaiting is made of natural silk.

8. A member as set forth in claim 1 wherein said rope has a plurality of said rings disposed in concentric relation with said filaments in each successive outer ring being of decreasing diameter outwardly of said core filament.

9. A member as set forth in claim 8 wherein said core filament has a diameter of between 0.1 to 1.0 millimeter and said outer filaments have a diameter of between 0.05 to 0.5 millimeters.

10. A member as set forth in claim 1 wherein each filament is made of a CoNi Cr MoTi—wrought alloy.

11. A member as set forth in claim 1 wherein said rope is longitudinally inelastic.

12. A member as set forth in claim 1 wherein said outer filaments are helically disposed about said core filament.

* * * * *

UNITED STATES PATENT AND TRADEMARK OFFICE
CERTIFICATE OF CORRECTION

PATENT NO. : 4,345,339
DATED : August 24, 1982
INVENTOR(S) : ARNOLD MULLER AND GERHARD BROCKEL It is certified that error appears in the above—identified patent and that said Letters Patent is hereby corrected as shown below:

Column 1, line 51, change "substitutes" to --substitute--

Signed and Sealed this

Sixteenth Day of November 1982

[SEAL]

Attest:

GERALD J. MOSSINGHOFF

Attesting Officer     Commissioner of Patents and Trademarks